US005541169A

United States Patent [19]
Deushi et al.

[11] Patent Number: 5,541,169
[45] Date of Patent: Jul. 30, 1996

[54] AZOXY COMPOUND

[75] Inventors: Takeo Deushi, Sayama; Yoshio Takahashi, Iruma; Hiroyuki Ishiwata, Ichikawa; Yukihiro Okuno; Toshiaki Oda, both of Higashimurayama; Masami Shiratsuchi, Musashimurayama; Katsuhiro Yamamoto, Higashimurayama, all of Japan

[73] Assignee: Kowa Company, Ltd., Aichi, Japan

[21] Appl. No.: 232,245

[22] PCT Filed: Sep. 10, 1993

[86] PCT No.: PCT/JP93/01295

§ 371 Date: May 10, 1994

§ 102(e) Date: May 10, 1994

[87] PCT Pub. No.: WO94/05629

PCT Pub. Date: Mar. 17, 1994

[30] Foreign Application Priority Data

Sep. 10, 1992 [JP] Japan .................................. 4-266827
Sep. 11, 1992 [JP] Japan .................................. 4-267955

[51] Int. Cl.⁶ ...................... A61K 31/655; A01N 51/00; C07C 291/08
[52] U.S. Cl. ...................... 514/149; 534/566; 534/572
[58] Field of Search ............................ 534/566; 514/149

[56] References Cited

U.S. PATENT DOCUMENTS

| 4,981,954 | 1/1991 | Nakayama et al. | 534/566 |
| 5,093,480 | 3/1992 | Nakayama et al. | 534/566 |
| 5,264,559 | 11/1993 | Nakayama et al. | 534/566 |

FOREIGN PATENT DOCUMENTS

| 0282001 | 9/1988 | European Pat. Off. . | |
| 0396769 | 11/1990 | European Pat. Off. . | |
| 0443513 | 8/1991 | European Pat. Off. | 534/566 |
| 3-240766 | 10/1991 | Japan . | |
| 1097255 | 1/1968 | United Kingdom . | |

OTHER PUBLICATIONS

Nelson et al., "Regiospecific Synthesis of Unsymmetrical Azoxy Compounds (Diazene N–Oxides)", J. Org. Chem., vol. 41, No. 10, 1976, pp. 1751–1754.

Luk'yanov et al., *Chemical Abstracts*, 112:55114 b (1990).

Nakata et al., "Regioselective Oxidation of β–Hydroxyazo Compounds to β–Hydroxyazoxy Compounds and Its Application to Syntheses of Maniwamycins A and B", *Tetrahedron Letters*, vol. 34, No. 38, Sep. 17, 1993, pp. 6095–6098.

Luk'yanov et al., *Izv. Akad. Nauk SSSR, Ser. Khim.* (1989), (5), 1110–1115.

*Primary Examiner*—Fiona T. Powers
*Attorney, Agent, or Firm*—Wenderoth, Lind & Ponack

[57] ABSTRACT

An azoxy compound represented by the following general formula $$R_1-\underset{}{\phenyl}-(C(R_2)=CH)_n-N=N(\to O)-CH(R_3)-CH(OR_4)-R_5 \quad (I)$$

wherein $R_1$ denotes a hydrogen atom, a halogen atom, a hydroxyl group, a lower alkoxy group, a lower alkoxy-lower alkoxy group or a group of the formula $X_1-C\equiv C-CH_2O-$ wherein $X_1$ is a hydrogen atom or a halogen atom;

$R_2$ denotes a hydrogen atom or a lower alkyl group;

$R_3$ denotes a hydrogen atom or a lower alkyl group;

$R_4$ denotes a hydrogen atom or a group of the formula $X_2-C\equiv C-CH_2-$ wherein $X_2$ is a hydrogen atom or a halogen atom;

$R_5$ denotes a hydrogen atom or a lower alkyl group; and $n$ is 0 or 1.

This compound has an excellent antifungal activity against fungi infectious to warm-blooded animals and fungi infectious to agrohorticultural crops or fruit trees, and is useful as a medicine, a veterinary drug and an agrohorticultural antifungal agent.

7 Claims, No Drawings

AZOXY COMPOUND

This application is a 371 of PCT/JP93/01295 filed Sep. 10, 1993.

TECHNICAL FIELD

This invention relates to a novel antifungal compound, and more particularly relates to a novel azoxy compound, a preparation process thereof and a use thereof as an antifungal agent.

BACKGROUND ART

It is already known that *Streptomyces* sp. KC-7367 (FERM BP-1277), a microorganism isolated from soil in Maniwa-gun, Okayama-prefecture, Japan produces two substances which are represented by the following formulae

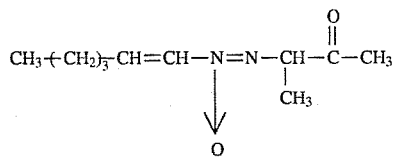

KA-7367A (Maniwamycin A)

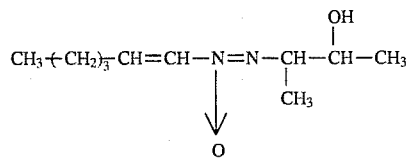

KA-7367B (Maniwamycin B)

and exhibit a strong antifungal activity against fungi (U.S. Pat. No. 4,981,954 and EP-B-282,001).

Further, it is also reported that the 2-imino derivative of KA-7367A obtained by imination of the carbonyl group at the 2-position of the above antifungal substance KA-7367A has a high antifungal activity (U.S. Pat. No. 5,093,480 and EP-B-396,769).

However, although the above compounds KA-7367A and B exhibit an excellent antifungal activity, KA-7367A is unstable, and although the 2-imino derivative of KA-7367A is improved in stability as a result of the imination, it has a difficulty that its antifungal activity is lowered compared with its parent compound KA-7367A.

As compounds to improve these problems, EP-A -443,513 (Japanese Laid-Open Patent Publication No. 240766/1991) discloses compounds represented by the following formula

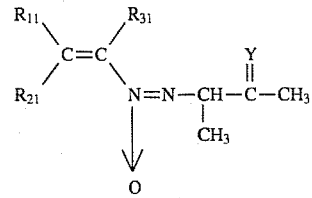

wherein $R_{11}$, $R_{21}$ and $R_{31}$ are the same or different with one another, and each represent a hydrogen atom, a halogen atom, an alkyl group, an alkenyl group, a haloalkyl group, an alkoxy group, an alkylthio group, an aryl or aralkyl group wherein the aromatic ring is optionally substituted by 1 to 3 substituents, or a hetero-cyclic group optionally substituted by 1 to 3 substituents, or $R_{11}$ and $R_{21}$ combine to form an alkylene group, Y denotes O or NOH provided that when $R_{21}$ (or $R_{11}$) and $R_{31}$ denote hydrogen atoms simultaneously, $R_{11}$ (or $R_{21}$) cannot denote an n-butyl group.

DISCLOSURE OF INVENTION

This invention provides an azoxy compound represented by the following general formula

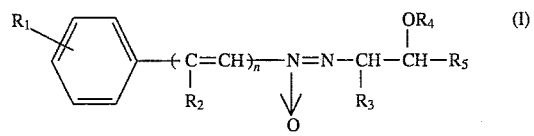

wherein $R_1$ denotes a hydrogen atom, a halogen atom, a hydroxyl group, a lower alkoxy group, a lower alkoxy-lower alkoxy group or a group of the formula $X_1$—C≡C—$CH_2O$— wherein $X_1$ is a hydrogen atom or a halogen atom;

$R_2$ denotes a hydrogen atom or a lower alkyl group;

$R_3$ denotes a hydrogen atom or a lower alkyl group;

$R_4$ denotes a hydrogen atom or a group of the formula $X_2$—C≡C—$CH_2$— wherein $X_2$ is a hydrogen atom or a halogen atom;

$R_5$ denotes a hydrogen atom or a lower alkyl group; and n is 0 or 1.

In this description, the term "lower" means that a group or compound to which this term is attached has 6 or less, preferably 4 or less carbon atoms.

The "halogen atom" includes the four atoms of fluorine, chlorine, bromine and iodine.

The "alkyl group" is a straight-chain or branched chain saturated aliphatic hydrocarbon group, and there can, for example, be mentioned methyl, ethyl, n- or iso-propyl, n- or iso- or tert-butyl, n-pentyl, isoamyl, n-hexyl, etc.

The "alkoxy group" is an (alkyl)-O-group wherein the alkyl moiety has the above meaning, and there can, for example, be mentioned methoxy, ethoxy, n- or iso-proproxy, n- or iso- or tert-butoxy, etc.

The "lower alkoxy-lower alkoxy group" is a lower alkoxy group substituted by a lower alkoxy group, and there can, for example, be mentioned methoxymethoxy, ethoxymethoxy, methoxyethoxy, ethoxyethoxy, etc.

As specific examples of the compounds of the above formula (I) provided by this invention, the following ones are mentioned besides those disclosed in the later-described examples.

3-(2-(2-hydroxyphenyl)-1-butenyl-ONN-azoxy)-2-butanol, 3-(2-(4-methoxyphenyl)-1-pentenyl-ONN-azoxy)-2-butanol, 3-(3-methyl-2-(4-tert-butoxyphenyl)-1-butenyl-Onn-azoxy)-2-butanol, 3-(2-phenyl-1-hexenyl-ONN-azoxy)-2-butanol, 3-(4-methyl-2-(4-ethoxyphenyl)-1-pentenyl-ONN-azoxy)-2-butanol, 3-(3,3-dimethyl-2-(4-n-propoxyphenyl)-1-butenyl-ONN-azoxy)-2-butanol, 3-(2-(4-iso-propoxyphenyl)-1-heptenyl-ONN-azoxy)-2-butanol, 3-(5-methyl-2-(4-n-butoxyphenyl)-1-hexenyl-ONN-azoxy)-2-butanol, 3-(2-(4-iso-butoxyphenyl)-1-octenyl-ONN-azoxy)-2-butanol, 1-(4-(3-bromo-2-propynyloxy)styryl-ONN-azoxy)-2-propanol, 3-(4-chlorostyryl-ONN-azoxy)-2-(2-propynyloxy)-butane, 3-(3-chlorostyryl-ONN-azoxy)-2-(3-iodo-2-propynyloxy)-butane, 2-(2-(3-chloro-2-propynyloxy)styryl-ONN-azoxy)-propanol, 2-(3-chlorostyryl-ONN-azoxy)-1-(3-iodo-2-propynyloxy)-propane, 3-(3- (3-iodo-2-propynyloxy)styryl-ONN-azoxy)-2-pentanol, 2-(styryl-ONN-azoxy)-ethanol, etc.

Particularly preferable among the compounds of this invention are compounds represented by the following formula

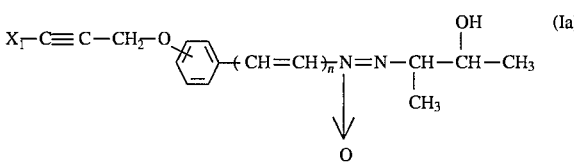

(Ia)

wherein $X_1$ is a halogen atom, particularly an iodine atom, and n is 0 or 1.

Particularly preferred compounds are 3-(4-(3-iodo-2-propynyloxy)styryl-ONN-azoxy)-2-butanol and 3-(4-(3-iodo-2-propynyloxy)phenyl-ONN-azoxy)-2-butanol.

The compounds of the above formula (I) sometimes have 1 or 2 asymmetric carbon atoms, and those having asymmetric carbon atom(s) can exist in a form of chiral compounds, diastereomers, racemates, their optional mixtures, etc. Further, when n is 1 in the formula (I), the compound of this invention can exist in a form of a cis-compound, a trans-compound or a mixture thereof based on the existing carbon-carbon double bond.

Among the compounds of the above formula (I) provided by this invention, a compound wherein $R_4$ is a hydrogen atom and n is 1 can, for example, be prepared by reduction of a compound represented by the following formula

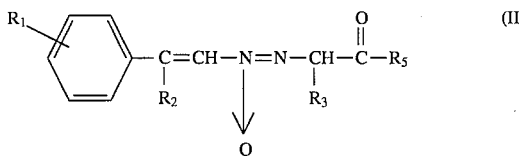

(II)

wherein $R_1$, $R_2$, $R_3$ and $R_5$ have the above-mentioned meanings.

The reduction of the compound of the formula (II) can appropriately be carried out in inert solvent, for example, an alcohol such as methanol, ethanol, propanol or isopropanol; an ether such as tetrahydrofuran, diethyl ether, dioxane or dimethoxyethane; acetonitrile, water, acetic acid or the like, according to a reduction with a metal hydride compound such as sodium borohydride, potassium borohydride or lithium aluminum hydride; a catalytic reduction using a hydrogenating catalyst comprising a metal such as platinum, nickel or palladium-carbon; an electrolytic reduction; or the like.

The compound of the formula (I) can be separated and purified from the reaction mixture according to methods known per se, for example, chromatography, crystallization, freeze-drying, extraction, etc.

Compounds of the formula (II) used as a starting material in the above reaction, part of which are known compounds, can, for example, be prepared by the following reaction formula in accordance with the process disclosed in EP-A-443,513 (Japanese Laid-Open Patent Publication No. 240766/1991).

Reaction formula A

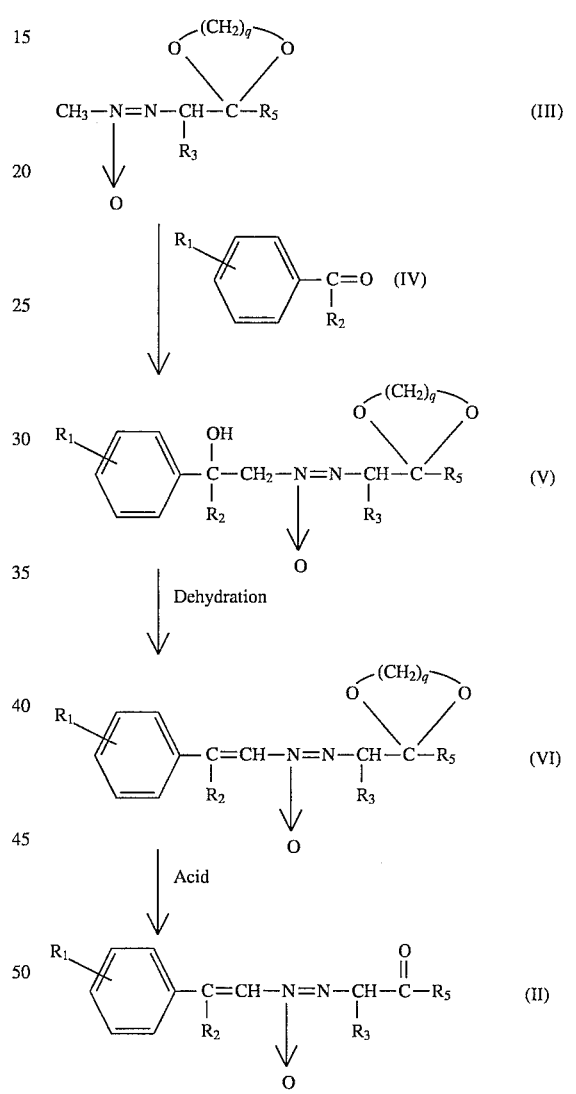

in the above reaction formula, $R_1$, $R_2$, $R_3$ and $R_5$ have the above-mentioned meanings, and q is 2 or 3.

Further, in the above reaction formula A, it is also possible to use a compound represented by the following formula

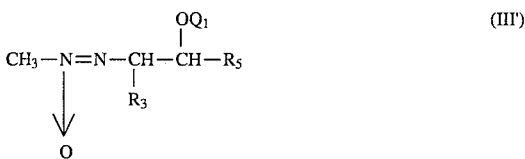

(III')

wherein, $R_3$ and $R_5$ have the above-mentioned meanings, and $Q_1$ denotes a protecting group for a hydroxyl group, for example, a tert-butyldimethylsilyl group, in place of the compound of the formula (III).

Reaction conditions for the respective steps in the above reaction formula A are disclosed in the above EP-A-443,513 (Japanese Laid-Open Patent Publication No. 240766/1991), and thus herein reference thereto is made as a substitute for detailed description thereof.

A compound of the formula (II) wherein R denotes a group of the formula $X_1'$—C≡C—$CH_2O$— (wherein $X_1'$ is a halogen atom) can also be prepared by halogenating a corresponding compound represented by the formula (V) or (VI), preferably the formula (VI) wherein $R_1$ denotes a group of the formula HC≡C—$CH_2O$— in the above reaction formula A, according to a process known per se, for example, using a halogenating agent such as a strong alkali-halogen, e.g. an alkali-iodine.

Further, among the compounds of the above formula (I) provided by this invention, a compound wherein $R_4$ is a hydrogen atom and n is 0, can, for example, be prepared by reacting a nitrobenzene derivative represented by the following formula

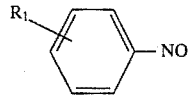   (VII)

wherein $R_1$ has the above-mentioned meaning, with an N,N-dihalogenated amine derivative represented by the following formula

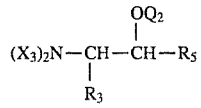   (VIII)

wherein $R_3$ and $R_5$ have the above-mentioned meanings, $Q_2$ denotes a hydrogen atom or a protecting group for a hydroxyl group, for example, a tert-butyldimethylsilyl group, and $X_3$ denotes a halogen atom, and then, if necessary, eliminating the protecting group for a hydroxyl group.

The above reaction can be carried out according to a conversion to an azoxy group known per se, for example, a procedure disclosed in P. Kovacic et al., J. Org. Chem., 41, 1751 (1976).

For example, the above reaction can be carried out by reaction a compound of the formula (VII) with a compound of the formula (VIII) in the presence of a metal salt as a reaction initiator at a temperature within the range of usually about −50° C. to about +50° C., preferably about −10° C. to room temperature for several hours to several days.

As the metal salt usable as the reaction initiator, there can be mentioned a metal salt of an inorganic or organic acid such as, for example, copper chloride, copper cyanide, potassium iodide, silver chloride, silver bromide, copper iodide, copper sulfide, iron chloride, iron sulfate, cobalt bromide, cobalt sulfate, silver cyanide or silver acetate. Such a metal salt can generally be used in the ratio of 1 to 3 moles, preferably 1.2 to 1.5 moles per mole of a compound of the formula (VII).

Further, the ratio of the compound of the formula (VIII) to the compound of the formula (VII) is not strictly limited, but it is usually suitable to use the compound of the formula (VIII) within the range of 0.5 to 1.5 moles, particularly 1 to 1.2 moles per mole of the compound of the formula (VII).

The above reaction can appropriately be carried out in a solvent, and as usable solvents, there can be mentioned solvents miscible with the starting material, for example, alcohols such as methanol and ethanol; ethers such as tetrahydrofuran, dioxane and diethyl ether; acetonitrile; etc., and solvents not sufficiently miscible with the starting material, for example, hydrocarbons such as benzene and toluene; halogenated hydrocarbons such as chloroform, carbon tetrachloride and methylene chloride; etc., but it is particularly preferable to use methanol, ethanol, acetonitrile, etc.

When in the above reaction, a compound of the formula (VIII) wherein $Q_2$ is a protecting group for a hydroxyl group is used, the protecting group can be eliminated from the reaction product according to an ordinary process, for example acid hydrolysis. As an acid usable therein, an inorganic acid such as hydrochloric acid or sulfuric acid is, for example, suitable.

It is also possible to use an amine compound represented by the following formula

wherein $R_3$, $R_5$ and $Q_2$ have the above-mentioned meaning, in place of the compound of the formula (VIII) in the above azoxy group-introducing reaction, and let an oxidizing agent and a halogen, preferably iodine act on this compound to form an N,N-dihalogenated amine derivative of the above formula (VIII) in situ in the reaction system, and let it react with the compound of the formula (VII).

As oxidizing agents usable in this reaction, there can, for example, be mentioned sodium hypochlorite, potassium hypochlorite, calcium hypochlorite, tert-butyl hypochlorite, etc. Such an oxidizing agent can usually be used in the ratio of 0.1 to 5 moles, particularly 1 to 3 moles per mole of the compound of the above formula (IX). Further, the halogen can generally be used within the range of 0.1 to 5 moles, preferably, 1 to 3 moles per mole of the compound of the formula (IX).

The thus formed compound of the above formula (I) can be separated and purified from the reaction mixture according to methods known per se, for example, methods such as chromatography, crystallization, freeze-drying, solvent extraction, etc.

A thus obtainable compound of the formula (I) wherein $R_1$ denotes a group of the formula HC≡C—$CH_2O$— can be converted to a compound of the formula (I) wherein the corresponding $R_1$ denotes a group of the formula $X_1$—C≡C—$CH_2O$— (wherein $X_1$ is a halogen atom) by halogenating the former compound according to a process known per se, for example using a halogenating agent such as a strong alkali-halogen, e.g. an alkali-iodine.

Further, a thus obtainable compound of the formula (I) wherein $R_4$ is a hydrogen atom can, for example, be converted to a compound of the formula (I) wherein $R_4$ denotes a group of the formula HC≡C—$CH_2$— by reacting the former compound with a propargyl halide represented by the following formula

   (X)

wherein $X_4$ denotes a halogen atom, in the presence of a base at a temperature of about −20° to about +50° C., and the resultant compound can further be converted to a compound of the formula (I) wherein $R_4$ denotes a group of the formula $X_2'$—C≡CH—$CH_2$ (wherein $X_2'$ is a halogen atom) by halogenating the former compound in the same manner as above-described.

The compounds of the above formula (I) of this invention have an excellent antifungal activity, and exhibit a remarkable antifungal activity against fungi infectious to warm-blooded animals including human beings such as, for example, the genus Candida, the genus Cryptococcus, the genus Aspergillus, the genus Trichophyton and the genus Microsporum; or fungi infectious to agrohorticultural crops such as, for example, the genus Pyricularia, the genus Botrytis, the genus Saccharomyces and the genus Septoria.

Table 1 shows the results of assay of the minimum inhibitory concentration (μg/ml) against fungi of representative compounds of this invention prepared in the later-described examples.

The minimum inhibition concentration was assayed by the agar plate dilution method using Sabouraud dextrose medium.

TABLE 1

| Example No. | Minimum inhibitory concentration (μg/ml) Test microorganism | | | |
|---|---|---|---|---|
| | C.a. | M.c. | T.r. | T.m. |
| 1 | 50 | 1.6 | 0.8 | 0.4 |
| 2 | 50 | 1.6 | 1.6 | 1.6 |
| 3 | 25 | 0.2 | 0.2 | — |
| 5 (2R) | 12.5 | 1.6 | 1.6 | 0.8 |
| 5 (2S) | 6.3 | 1.6 | 1.6 | 0.8 |
| 11 | 6.3 | 0.8 | 1.6 | 1.6 |
| 17 | 6.3 | 0.8 | 1.6 | 1.6 |

*C.a.: *Candida albicans*
M.c.: *Microsporum canis*
T.r.: *Trichophyton rubrum*
T.m.: *Trichophyton mentagrophytes*

Further, Table 2 shows the results of measurement of the stability of representative compounds of this invention in ethanol in comparison with a representative compound disclosed in the above EP-A-443,513.

The residual ratio was determined under the following conditions by the HPLC method.

TABLE 2

| | | Residual ratio (%)* | | | | |
|---|---|---|---|---|---|---|
| | Example No. | 5 (2R) | 5 (2S) | 17 | | Control** |
| Preserving condition | Preserving period | 3 months | 3 months | 12 days | 3 months | 12 days |
| 4° C. | | 99.6 | 99.8 | 100.3 | 100.4 | 99.3 |
| 25° C. | | 99.3 | 97.4 | 101.5 | 99.4 | 95.8 |
| 40° C. | | 92.7 | 86.1 | 99.8 | 100.3 | 96.6 |
| pH 4 | 40° C. | 101.3 | 100.5 | 99.7 | 100.4 | 0 |
| pH 6 | 40° C. | 100.6 | 99.1 | 100.3 | 99.9 | 79.7 |
| pH 8 | 40° C. | 83.6 | 74.2 | 100.3 | 100.4 | 91.4 |

*Measured in a 50% ethanol solution (sample concentration: 0.01%)
HPLC condition:
Column: STR ODS-M 4.6 × 150 mm
Injection volume: 40 μl
Mobile phase: CH$_3$CN:H$_2$O (1:1)
Temperature: room temperature
Flow rate: 1 ml/min
Detection: UV254 nm
**Control compound

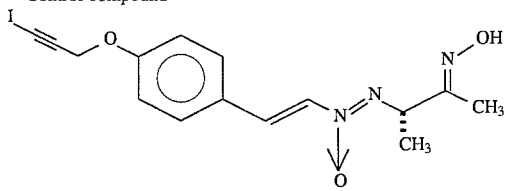

As stated above, the compounds of this invention have an excellent antifungal activity against fungi infectious to warm-blooded animals including human beings or fungi infectious to agrohorticultural crops or fruit trees, and are useful as an antifungal agent for medicines, veterinary drugs and agrohorticulture for treatment of mycetogenic infectious diseases on warm-blooded animals or treatment of agrohorticultural crops or fruit trees infected with fungi, or the like.

The compounds of this invention, when used as an antifungal agent, can be formulated into forms suitable for their respective uses and used. For example, when a compound of this invention is used as a medicine or a veterinary drug (animal drug), the compound can be formulated into a dosage form for oral administration, injection, rectal administration, external use, or the like by adding pharmaceutically acceptable auxiliaries such as an excipient, a binder, a disintegrant, a coating agent, an emulsifier, a suspending agent, a solvent, a stabilizer, an absorption auxiliary and an ointment base, according to necessity, and formulating the mixture according to a conventional process.

As preparations for oral administration, there can, for example, be mentioned granules, tablets, sugar-coated tablets, capsules, pills, liquids, emulsions, suspensions, etc., and as preparations for injection administration, there can, for example, be mentioned preparations for intravenous injection, intramuscular injection, subcutaneous injection and drip injection, etc., and as preparations for rectal administration, there can, for example, be mentioned suppositories, soft capsules, etc. As external agents, ointments, lotions, liniments, creams, etc. are preferable. Further, dosage forms of eye drops, ear drops, etc. can also be utilized.

When a compound of this invention is used as an antifungal agent for agrohorticulture, the compound can be formulated into a dosage form such as an emulsion, granules, powder, dust or paste according to a conventional process.

The dose of a compound of this invention when administered to warm-blooded animals including human beings can widely be varied depending on the kind of animals to be administered, the seriousness of symptoms, weight, sex, judgment of the doctors who make the treatment, etc., but is usually within the range of about 0.1 to about 500 mg/kg weight per day, and such dose can be administered once a day or in several divided portions per day.

Further, for agrohorticultural uses, a compound of this invention can be applied to an area where fungi live, for soil treatment, stems and leaves treatment, etc., and its application quantity is usually within the range of about 0.005 to about 5 kg/ha.

EXAMPLES

This invention is further specifically described below by examples. Starting compounds shown in reference examples can be obtained as an optically active azoxymethyl compound by using their corresponding optically active raw materials.

Reference Example 1

Preparation of 2-(methyl-ONN-azoxy)-1-(tert-butyldimethylsilyloxy)propane

2-Amino-1-propanol was subjected to N-ethoxycarbonylation and O-tert-butyldimethylsilylation by conventional methods to give 2-ethoxycarbonylamino-1-tert-butyldimethylsilyloxy-propane (compound 1), which was then subjected to reaction according to the procedure for preparation of 3-(methyl-ONN-azoxy)-2,2-propylenedioxybutane disclosed in EP-A-443,513 (Japanese Laid-Open Patent Publication No. 240766/1991) to give the desired compound as a pale yellow oily matter. Total yield from compound 1:38%.

$^1$H-NMR (CDCl$_3$, δ) 0.52 (6H, s, SiCH$_3$), 0.88 (9H, s, Si-t-Bu), 1.10 (3H, d, J=6 Hz, 3-CH$_3$), 3.63 (1H, dd, J=10 Hz, 6 Hz, 1-CH), 3.74 (1H, dd, J=10 Hz, 6 Hz, 1-CH), 4.05 (3H, s, =N—CH$_3$), 4.16 (1H, sext., J=6 Hz, 2-CH).

Optically active 2-(methyl-ONN-azoxy)-1-(tertbutyldimethylsilyloxy)propane can be obtained by reduction an optically active ester of N-benzyloxycarbonylalanine to give an alcohol, and then tert-butyldimethylsilylating the alcohol.

Example 1

Preparation of 2-(2-(4-chlorophenyl)-1-propenyl-ONN-azoxy)-1-(3-iodo-2-propynyloxy)propane (a) 251.6 mg (1.08 mmol) of the optically active azoxymethyl compound of Reference example 1 was subjected to condensation reaction with parachloroacetophenone and dehydration reaction according to the procedure disclosed in EP-A-443,513 (Japanese Laid-Open Patent Publication No. 240766/1991) to give 33.6 mg of 2-(2-(4-chlorophenyl)-1-propenyl-ONN-azoxy)-1-(tert-butyldimethylsilyloxy)propane as a colorless oil (yield 8.6%).

$^1$H-NMR (CDCl$_3$, δ) 0.07 (6H, s, SiCH$_3$), 0.89 (9H, s, Si-t-Bu), 1.20 (3H, d, J=6 Hz, 3-CH$_3$), 2.43 (3H, d, J=2 Hz, 3'-CH$_3$), 3.62 (1H, dd, J=10 Hz, 6 Hz, 1-CH), 3.73 (1H, dd, J=10 Hz, 6 Hz, 1-CH), 4.33 (1H, sext., J=6 Hz, 2-CH), 7.04 (1H, q, J=2 Hz, 1'—CH=), 7.36 (4H, s, Aromatic H).

(b) 28.8 mg (0.0782 mmol) of the propane compound obtained in the above (a) was dissolved in 0.4 ml of methanol, 0.1 ml of 1N hydrochloric acid was added, and the mixture was stirred at room temperature for 15 minutes. After the reaction, the reaction mixture was diluted with water, followed by extraction with ethyl acetate. The organic layer was washed successively with saturated saline, saturated sodium bicarbonate solution, saturated ammonium chloride solution and saturated saline, dried over anhydrous sodium sulfate, and then concentrated under reduced pressure. The residue was purified by silica gel preparative thin layer chromatography (diethyl ether-hexane=2:1) to give 17.7 mg (yield 89%) of 2-(2-(4-chlorophenyl)-1-propenyl-ONN-azoxy)-1-propanol as a colorless oil.

$^1$H-NMR (CDCl$_3$, δ) 1.22 (3H, d, J=6 Hz, 3-CH$_3$), 2.00 (1 H, brs, —OH), 2.46 (3H, d, J=2 Hz, 3'-CH$_3$), 3.80 (2H, d, J=6 Hz, 1-CH$_2$), 4.38 (1H, sext, J=6 Hz, 2-CH$_4$), 7.09 (1H, q, J=2 Hz, 1'—CH=), 7.37 (4H, s, Aromatic H).

IR value:ν max, CHCl$_3$, cm$^{-1}$ 3420 (br), 1460, 1315, 1095, 1010.

(c) 17.7 mg (0.0695 mmol) of the propanol compound obtained in the above (b) was dissolved in 0.5 ml of anhydrous dimethylformamide under an argon stream, 0.06 ml (0.065 mmol) of propargyl bromide and 10 mg (0.208 mmol) of 50% sodium hydride were added under cooling by an ice bath using a refrigerant, and the mixture was stirred for 30 minutes. After the reaction, saturated saline was added to the reaction solution at that temperature, and diethyl ether was added to carry out extraction. The organic layer was washed successively with saturated saline, saturated ammonium chloride solution and saturated saline, dried over anhydrous sodium sulfate, and concentrated under reduced pressure. The resultant residue was purified by silica gel preparative thin layer chromatography (ethyl acetate-benzene =1:50) to give 8.6 mg of 2-(2-(4-chlorophenyl)-1-propenyl-ONN-azoxy)-1-(2-propynyloxy)propane as a colorless oil (yield 42%).

$^1$H-NMR (CDCl$_3$, δ) 1.24 (3H, d, J=6 Hz, 3-CH$_3$), 2.44 (1H, t, J=3 Hz, ≡CH), 2.45 (3H, d, J=2 Hz, 3'-CH$_3$), 4.20 (1H, dd, J=10 Hz, 5 Hz, 1-CH), 4.22 (2H, d, J=3 Hz, 0-CH$_2$C≡), 4.26 (1H, dd, J=10 Hz, 7 Hz, 1-CH), 4.38-4.56 (1H, m, 2-CH), 7.09 (1H, q, J=2 Hz, 1'-CH=), 7.36 (4H, s, Aromatic H).

IR value:ν max, CHCl$_3$, cm$^{-1}$ 3290, 1460, 1315, 1095, 1030.

(d) 8.9 mg (0.04 mmol) of the O-propargyl compound obtained in the above (c) was dissolved in 0.4 ml of methanol, and under ice cooling, 0.01 ml (0.1 mmol) of 10N sodium hydroxide solution and 35.1 mg (0.138 mmol) of iodine were added. When the reaction solution became a uniform solution, cooling was stopped and the reaction solution was stirred at room temperature for 10 minutes. After the reaction, diethyl ether was added to the reaction solution to carry out extraction. The organic layer was washed with 1M sodium thiosulfate solution and saturated saline, dried over anhydrous sodium sulfate, and concentrated under reduced pressure. The resultant residue was purified by silica gel preparative thin layer chromatography (ethyl acetate-benzene=1:10) to give 6.6 mg of the desired compound as a colorless oil (yield 76%).

$^1$H-NMR (CDCl$_3$, δ) 1.23 (3H, d, J=6 Hz, 3-CH$_3$), 2.45 (3H, d, J=2 Hz, 3'-CH$_3$), 4.18 (1H), dd, J=10 Hz, 5 Hz, 1-CH), 4.25 (1H, dd, J=10 Hz, 6 Hz, 1-CH), 4.36 (2H, s, OCH$_2$C≡), 4.36–4.56 (1H, m, 2-CH), 7.09 (1H, q, J=2 Hz, 1'—CH═), 7.36 (4H, s, aromatic H).

IR value:ν max, CHCl$_3$, cm$^{-1}$ 1460, 1315, 1095, 1010.

Example 2

Preparation of 3-(2-(2-chlorophenyl)-1-propenyl-ONN-azoxy)-2-(3-iodo-2-propynyloxy)butane (a) 3-(2-(2-chlorophenyl)-1-propenyl-ONN-azoxy)-2,2-propylenedioxybutane disclosed in EP-A-443,513 was subjected to deketalization according to a conventional process, and the product was then reduced with sodium borohydride to give 40.6 mg of 3-(2-(2-chlorophenyl)-1-propenyl-ONN-azoxy)-2-butanol as a colorless oil (yield 60%).

$^1$H-NMR (CDCl$_3$, δ) (Mixture of diastereomer.) 1.20, 1.21 (Total 3H, d, J=7 Hz, 1 or 4-CH$_3$), 1.26 (3H, d, J=7 Hz, 1 or 4-CH$_3$), 2.45 (3H, d, J=2 Hz, 3'-CH$_3$), 3.87–4.27 (2H, m, 2 and 3-CH), 6.85, 6.86 (Total 1H, q, J=2 Hz, 1'—CH═), 7.22–7.46 (4H, m, Aromatic H).

IR value: ν max, CHCl$_3$, cm$^{-1}$ 3450, 1465, 1370, 1315, 1040.

(b) 20.5 mg (0.076 mmol) of the butanol compound obtained by the above (a) was dissolved in 0.5 ml of anhydrous dimethylformamide under an argon stream, 0.11 ml (1.2 mmol) of propargyl bromide and 19 mg (0.0396 mmol) of 50% sodium hydride were added under cooling by an ice bath using a refrigerant, and the mixture was stirred for 30 minutes. After the reaction, saturated saline was added to the reaction solution at that temperature, and diethyl ether was added to carry out extraction. The organic layer was washed with saturated saline, saturated ammonium chloride solution and saturated saline, dried over anhydrous sodium sulfate, and concentrated under reduced pressure. The resultant residue was purified by silica gel preparative thin layer chromatography (ethyl acetate-benzene=1:30) to give 4.2 mg (yield 18%) of 3-(2-(2-chlorophenyl)-1-propenyl-ONN-azoxy)-2-(2-propynyloxy)butane as a colorless oil. This compound was reacted in the same manner as in Example 1-d to give 4.3 mg of the desired compound as a colorless oil (yield 71%).

$^1$H-NMR (CDCl$_3$, δ) (Mixture of diastereomer.) 1.20, 1.26 (Total 3H, d, J=7 Hz, 1 or 4-CH$_3$), 1.22 (3H, d, J=7 Hz, 1 or 4-CH$_3$), 2.95, 2.96 (Total 3H, d, J=2 Hz, 3' -CH$_3$), 3.74–3.93 (1H, m, 2-CH), 4.23–4.55 (3H, m, 3-CH and 0-CH$_2$C≡), 6.85, 6.86 (Total 1H, q, J=2 Hz, 1' -CH═), 7.23–7.45 (4H, m, Aromatic H).

IR value:ν max, CHCl$_3$, cm$^{-1}$ 1465, 1370, 1315, 1070.

Example 3

Preparation of 3-(4-(2-propynyloxy)styryl-ONN-azoxy)-2-butanol 44.39 g (134.4 mmol) of 3-(4-(2-propynyloxy)-styryl-ONN-azoxy)-2,2-propylenedioxybutane, a compound disclosed in EP-A-443,513 was subjected to deketalization reaction with iron chloride-silica gel according to the process disclosed in EP-A-443,513 to give 38.94 g of a crude product of 3-(4-(2-propynyloxy)styryl-ONN-azoxy)-2-butanone as a colorless paste. This was dissolved in a mixed solvent of 80 ml of dimethylformamide and 240 ml of methanol, 5 g (134.4 mmol) of sodium borohydride was added, and the mixture was stirred under ice cooling for 1 hour. After the reaction, 300 ml of water and 200 ml of ethyl acetate were added to the reaction solution to carry out extraction. The organic layer was washed with saturated saline, dried over anhydrous sodium sulfate, and concentrated under reduced pressure. The residue was purified by silica gel chromatography (diethyl ether-hexane =2:1) to give 30.75 g of the desired compound as a colorless paste (yield 83%).

$^1$H-NMR (CDCl$_3$, δ) (Mixture of diastereomer.) 1.19, 1.20 (Total 3H, each d, J=6.5 Hz, 6.8 Hz, 1 or 4-CH$_3$), 1.25 (3 H, d, J=6.3 Hz, 1 or 4-CH$_3$), 2.18 (1H, br. s, OH), 2.55(1H, t, J=2.5 Hz, ≡CH), 3.94, 4.24 (Total 1H, each dt, each J=13.2 Hz, 6.5 Hz, J=10.8 Hz, 6.8 Hz, 2-CH), 4.12, 4.27 (Total 1H, each dt, J=13.2 Hz, 6.5 Hz, J=10.8 Hz, 6.8 Hz, 3-CH), 4.73 (2H, d, J=2.5 Hz, 0CH$_2$C≡), 6.70, 7.00, 7.46 (Total 4H, d, J=8.7 Hz, Aromatic H), 7.49, 7.50, 7.77, 7.78 (Total 2H, d, J=13.5 Hz, —C═CH—).

Example 4

3- (4- ( 2-propynyloxy)styryl-ONN-azoxy)-2-butanol obtained in Example 3 was separated into the respective optically active substances.

2 (R)-3(S) -3-(4-(2-propynyloxy) styryl-ONN-azoxy)-2-butanol $^1$H-NMR (CDCl$_3$, δ) 1.20 (3H, d, J=6.8 Hz, 1 or 4-CH$_3$), 1.25 (3H, d, J=6.3 Hz, 1 or 4-CH$_3$), 2.17 (1H, br, s, OH), 2.55 (1H, t, J=2.5 Hz, ≡CH), 4.24 (1H, dt, J=10.8 Hz, 6.8 Hz, 2-CH) , 4.27 (1H, dt, J=13.2 Hz, 6.5 Hz, 3-CH), 4.73 (2H, d, J =2.5 Hz, 0-CH$_2$C≡), 6.70 (2H, d, J=8.7 Hz, Aromatic H), 7.46 (2H, d, J =8.7 Hz, Aromatic H), 7.49 (1H, d, J=13.5 Hz, 1' or 2' —CH═), 7.78(1H, d, J=13.5 Hz, 1' or 2'—CH═) .

$[α]_D^{22}$+13.1° (c=1, CHCl$_3$)

IR value: ν max, CHCl$_3$, cm$^{-1}$ 3291, 2968, 1637, 1602, 1507, 1456.

2(S)-3(S)-3-(4-(2-propynyloxy)styryl-ONN-azoxy)-2-butanol $^1$H-NMR (CDCl$_3$, δ) 1.19 (3H, d, J=6.5 Hz, 1 or 4-CH$_3$), 1.25 (3H, d, J=6.3 Hz, 1 or 4-CH$_3$), 2.20 (1H, br. s, OH), 2.55 (1H, t, J=2.5 Hz, ≡CH), 3.94 (1H, br. dt, J=13.2 Hz, 6.5 Hz, 2-CH), 4.12 (1H, dt, J=13.2 Hz, 6.5 Hz, 3-CH), 4.73 (2H, d, J=2.5 Hz, 0-CH$_2$C≡), 7.00 (2H, d, J=8.7 Hz, Aromatic H), 7.46 (2H, d, J=8.7 Hz, Aromatic H), 7.50 (1H, d, J=13.5 Hz, 1' or 2' -CH═), 7.77 (1H, d, J=13.5 Hz, 1' or 2' -CH═) .

$[α]_D^{22}$+60.7° (c=1, CHCl$_3$)

IR value: ν max, CHCl$_3$, cm$^{-1}$ 3292, 2900, 1640, 1602, 1507, 1456.

Example 5

Preparation of 3-(4-(3-iodo-2-propynyloxy)styryl-ONN-azoxy)-2-butanol

The optically active propynyloxystyryl compound obtained in Example 4 was iodinated using the process of Example 1-d. 2(R)-3(S)-3-(4-(3-iodo-2-propynyloxy)styryl-ONN-azoxy)-2-butanol $^1$H-NMR (CDCl$_3$, δ) 1.21 (3H, d, J=6.5 Hz, 1 or 4-CH$_3$), 1.26(3H, d, J=6.5 Hz, 1 or 4-CH$_3$), 2.08 (1H, d, J=5 Hz, 2-0H), 3.96–4.06 (1H, m, 2-CH), 4.26 (1H, dq, J= 6.5 Hz, 4 Hz, 3-CH), 4.86 (2H, s, O-CH$_2$C≡), 6.98 (2H, d, J=8.8 Hz, Aromatic H), 7.46 (2H, d, J=8.8 Hz, Aromatic H), 7.49 (1H, d, J=14.2 Hz, 1' or 2'-0 -CH=),
7.77 (1H, d, J=14.2 Hz, 1' or 2' -CH=).

$[\alpha]_D^{21}$+7.8° (c=1, CHCl$_3$)

IR value:ν max, CHCl$_3$, cm$^{-1}$ 1449.

2(S)-3(S)-3-(4-(3-iodo-2-propynyloxy)styryl-ONN-azoxy)-2-butanol $^1$H-NMR (CDCl$_3$, δ) 1.19 (3H, d, J=6.5 Hz, 1 or 4-CH$_3$), 1.26 (3H, d, J=6.5 Hz, 1 or 4-CH$_3$), 2.14 (1H, d, 2-OH), 3.94 (1H, sext., J=6.4 Hz, 2-CH), 4.13(1H, quint., J=6.5 Hz, 3-CH), 4.86 (2H, s, 0-CH$_2$C≡), 6.98 (2H, d, J=8.8 Hz, Aromatic H), 7.47 (2H, d, J=8.8 Hz, Aromatic H), 7.51 (1H, d, J=14.2 Hz, 1' or 2' -CH=), 7.77 (1H, d, J=14.2 Hz, 1' or 2' -CH=).

$[\alpha]_D^{22}$+47.7° (c=1, CHCl$_3$)

IR value:ν max, CHCl$_3$, cm$^{-1}$ 1456.

Reference Example 2

Preparation of
3-amino-2-(tert-butyldimethylsilyloxy)butane (a) 2.4 g (20 mmol) of 3-nitro-2-butanol was dissolved in 10 ml of dimethylformamide, 4.08 g (60 mmol) of imidazole and 4.52 g (30 mmol) of tert-butyldimethylsilyl chloride were added under ice cooling, and the mixture was stirred at room temperature for 6 hours. After the reaction, the reaction solution was poured into 100 ml of ice water, and the mixture was extracted with diethyl ether. The organic layer was washed successively with 2N hydrochloric acid, saturated sodium bicarbonate solution and saturated saline, dried over anhydrous sodium sulfate, and concentrated under reduced pressure. The residue was purified with silica gel column chromatography (hexane-benzene=10:1) to give 4.73 g of 3-nitro-2-(tert-butyldimethylsilyloxy)butane as a colorless oil (yield: quantitative).

$^1$H-NMR (CDCl$_3$:δ) 0.01, 0.02 (Total 6H, each s, SiCH$_3$), 0.84, 0.86 (Total 9H, each s, Si-t-Bu), 1.18, 1.20 (Total 3H, each d, each J=6.3 Hz, 6 Hz, 1 or 4-CH$_3$), 1.45, 1.47 (Total 3H, each d, each J=6.8 Hz, 6.3 Hz, 1 or 4-CH$_3$), 4.12–4.24 (1H, m), 4.34–4.51 (1H, m).

IR:ν max, Neat, cm$^{-1}$ 2925, 1540, 1459.

(b) 1.0 g of the silyl compound obtained in the above (a) was dissolved in 10 ml of methanol, 100 mg of 10% palladium-carbon was added, and the mixture was stirred under a hydrogen stream at room temperature overnight. After the reaction, the catalyst was removed by filtration using Celite as a filter aid, and the filtrate was concentrated under reduced pressure to give 0.83 g of the desired compound (yield 95%).

$^1$H-NMR (CDCl$_3$:δ) 0.06, 0.07 (Total 6H, each s, SiCH$_3$), 0.89, 0.90 (Total 9H, each s, Si-t-Bu), 0.99, 1.02, 1.05, 1.11 (Total 6H, each d, each J=6.8 Hz, 6.8 Hz, 6.3 Hz, 6.3 Hz, 1 or 4-CH$_3$), 2.64–2.74, 2.78–2.88 (Total 1H, each m), 3.44–3.54, 3.62–3.70 (Total 1H, each m).

IR:ν max, Neat, cm$^{-1}$ 3350, 2949, 1251.

Reference Example 3

Preparation of
3-amino-2-(tert-butyldimethylsilyloxy)butane:

(a) Cis- and trans-2-butene oxides were ring-opened with ammonia, respectively to give 3-amino-2-butanol as a racemate.

(b) The above 3-amino-2-buanol was subjected to N-benzyloxycarbonylation and O-tert-butyldimethylsilylation, and then to catalytic reduction, according to conventional processes, to give 3-amino-2-(tert-butyldimethylsilyloxy)butane as a racemate.

Reference Example 4

Preparation of
2(R)-3(S)-3-amino-2-(tert-butyldimethylsilyloxy)butane (a) 7 g (78 mmol) of (2 R,3 R)-(–)-2,3-butanediol was dissolved in 80 ml of carbon tetrachloride, 6.8 ml (93 mmol) of thionyl chloride was added, and the mixture was refluxed with heating at 95° C. for 30 minutes. After the reaction, the mixture was cooled in an ice bath, 80 ml of acetonitrile, 160 mg (780 mmol) of ruthenium (III) chloride trihydrate, 25.4 g (117 mmol) of sodium metaperiodate and 120 ml of water were added successively, and the mixture was stirred at room temperature for 3 hours. The reaction solution was extracted with diethyl ether, the organic layer was washed with water, saturated sodium bicarbonate solution and saturated saline, dried over anhydrous sodium sulfate and anhydrous magnesium sulfate, and concentrated under reduced pressure. The residue was purified by vacuum distillation to give 11.36 g (bp. 95° C./4.5 mmHg) of a cyclic sulfonyl ester 4(R)-5(R)-4,5-dimethyl-1,3,2-dioxathiolane-3,3-dioxide as a colorless oil (yield 96%).

$^1$H-NMR (CDCl$_3$:δ) 1.51 (3H, d, J=2 Hz, CH$_3$), 1.52 (3H, d, J=1.5 Hz, CH$_3$), 4.64–4.70 (2 H,m).

(b) 15.0 g (99 mmol) of the above cyclic sulfonyl ester compound was dissolved in 20 ml of dimethylformamide, 10 g (149 mmol) of sodium azide was added, and the mixture was stirred at 80° C. for 30 minutes. After the reaction, the reaction solution was concentrated under reduced pressure, the residue was dissolved in 300 ml of diethyl ether-20% sulfuric acid (1:1), and the mixture was stirred at room temperature for 27.5 hours. After the reaction, the aqueous layer was extracted with methylene chloride, and the organic layer was washed successively with saturated sodium bicarbonate solution and saturated saline, dried over anhydrous magnesium sulfate and anhydrous sodium sulfate, and concentrated under reduced pressure. The residual azidoalcohol compound as a colorless oil was dissolved in 100 ml of dimethylformamide, 7.4 g (99 mmol) of imidazole and 15.0 g (99 mmol) of tert-butyldimethylsilyl chloride were added, and the mixture was stirred at room temperature for 3 hours. After the reaction, the reaction solution was stirred after addition of water, and extracted with diethyl ether. The organic layer was washed with water and saturated saline, dried over anhydrous magnesium sulfate and anhydrous sodium sulfate, and concentrated under reduced pressure. The residue was purified by silica gel column chromatography (diethyl ether-hexane=1:5) to give 10.7 g of (2 R, 3 S)-3-azido-2-(tert-butyldimethylsilyloxy)butane as a colorless oil (yield 46%).

$^1$H-NMR (CDCl$_3$:δ) 0.07 (3H, s, SiCH$_3$), 0.08 (3H, s, SiCH$_3$), 0.90 (9H, s, Si-t-Bu), 1.14 (3H, d, J=6.4 Hz, 1 or 4-CH$_3$), 1.17 (3H, d, J=6.4 Hz, 1 or 4-CH$_3$), 2.98–3.39 (1H, m), 3.73 (1H, m).

(c) 2.7 g (12 mmol) of the azidosilyl compound obtained in the above (b) was dissolved in 12 ml of methanol, 55 mg of 10% palladium-carbon was added thereto, and catalytic reduction was carried out under a hydrogen stream for 2 days. After the reaction, the catalyst was removed from the reaction solution by filtration using Celite as a filter aid, and the filtrate was concentrated under reduced pressure to give 2.4 g of the desired compound as a colorless solid (yield 100%).

$^1$H-NMR (CDCl$_3$:δ) 0.10 (3H, s, SiCH$_3$), 0.15 (3H, s, SiCH$_3$), 0.90 (9H, s, Si-t-Bu), 1.22 (3H, d, J=6.3 Hz, 1 or 4-CH$_3$), 1.35 (3H, d, J=6.8 Hz, 1 or 4-CH$_3$), 3.23–3.32 (1H, m), 4.00–4.09 (1H, m), 8.10–8.35(2H, br, s).

Example 6

Preparation of 3-(phenyl-ONN-azoxy)-2-butanol (a) 60 mg (0.3 mmol) of the silylamine compound obtained in Reference example 2 and 168 mg (0.66 mmol) of iodine were dissolved in 3 ml of benzene, 32 mg (0.3 mmol) of nitrosobenzene and 0.074 ml (0.66 mmol) of tert-butyl hypochlorite were added under ice cooling, and the mixture was stirred at room temperature overnight. After the reaction, 1M sodium thiosulfate solution was added to the reaction solution, followed by extraction with benzene. The organic layer was washed with saturated saline, dried over anhydrous sodium sulfate, and concentrated under reduced pressure. The residue was purified by silica gel column chromatography (hexane-benzene =1:1) to give 63 mg of 3-(phenyl-ONN-azoxy)-2-(tert-butyldimethylsilyloxy)butane as a colorless oil (yield 69%).

$^1$H-NMR (CDCl$_3$:δ) 0.05, 0.07, 0.07, 0.09 (Total 6H, each s, SiCH$_3$), 0.86, 0.89 (Total 9H, each s, Si-t-Bu), 1.19, 1.21, 1.22, 1.23 (Total 6H, each d, each J=6.3 Hz, 6.3 Hz, 6.0 Hz, 6.0 Hz, 1 or 4-CH$_3$), 4.03–4.14, 4.21, 4.35 (Total 2H, each m, quint., quint., J=6.0 Hz, 6.0 Hz, 2 and 3-CH), 7.42–7.56 (3H, m, Aromatic H), 8.15(2H, m, Aromatic H).

I R:v max, CHCl$_3$, cm$^{-1}$ 2940, 1477, 1435.

(b) 660 mg (2.14 mmol) of the azoxysilyl compound obtained in the above (a) was dissolved in 10 ml of methanol, 1.07 ml of 2N hydrochloric acid was added under ice cooling, and the mixture was brought back to room temperature and stirred for 3 hours. After the reaction, the reaction solution was poured into 50 ml of ice water, followed by extraction with ethyl acetate. The organic layer was washed with saturated sodium bicarbonate solution and saturated saline, dried over anhydrous sodium sulfate, and concentrated under reduced pressure. The residue was purified by silica gel column chromatography (ether-hexane= 1:1) to give 460 mg of the desired compound as a colorless oil (yield: quantitative).

$^1$H-NMR (CDCl$_3$:δ) 1.24, 1.26, 1.28, 1.29 (Total 6H, each d, each J=6.3 Hz, 6.8 Hz, 6.0 Hz, 6.3 Hz, 1 or 4-CH$_3$), 2.16 (1H, hr. d, J=13 Hz, OH), 3.97–4.12, 4.21, 4.29–4.38 (Total 2H, each m, quint., m, J=6.8 Hz, 2 and 3-CH), 7.42–7.56 (3H, m, Aromatic H), 8.15 (2H, m, Aromatic H).

I R:v max, Neat, cm$^{-1}$ 3400, 2966, 1478, 1439.

Example 7

Preparation of 3-(4-methoxymethoxyphenyl-ONN-azoxy)-2-butanol (a) 5.2 g (30 mmol) of 4-bromophenol was dissolved in 20 ml of anhydrous methylene chloride, and 1.6 g (5.9 mmol) of tetrabutylammonium chloride and 20 ml (50 mmol) of 2.5N sodium hydroxide solution were added successively under ice cooling and stirring. Further, 3.4 ml (45 mmol) of chloromethyl methyl ether was added, and the mixture was brought back to room temperature and stirred for 30 minutes. After the reaction, diethyl ether was added to the reaction solution to carry out extraction, and the organic layer was washed successively with water, 1N sodium hydroxide solution, saturated saline, saturated ammonium chloride solution and saturated saline, dried over anhydrous sodium sulfate, and concentrated under reduced pressure. Thereby, 5.7 g of 4-methoxymethoxybromobenzene was obtained as a colorless oil (yield 87%).

$^1$H-NMR (CDCl$_3$:δ) 3.46 (3H, s, OCH$_3$), 5.15 (2H, s, OCH$_2$O), 6.94.(2H, d,J=9 Hz, Aromatic 3, 5-H), 7.38 (2H, d,J=9 Hz, Aromatic 2, 6-H).

(b) A small quantity of iodine was put in a vessel containing 2.5 g (103 mmol) of metal magnesium and 90 ml of anhydrous tetrahydrofuran, and a solution of 20 g (92 mmol) of 4-methoxymethoxybromobenzene obtained in the above (a) in 90 ml of anhydrous tetrahydrofuran was gradually added dropwise under stirring. Reaction progressed rapidly, and after the reaction somewhat calmed down, the mixture was stirred at 50° C. for further 3 hours. Thereafter, the rector was cooled to 0° C., 22 g (110 mmol) of trimethyltin chloride was added thereto, and the mixture was heated again to 50° C. and refluxed for 2 hours. After the reaction, the reaction solution was cooled again to 0° C., saturated ammonium chloride solution was added, and the mixture was extracted with diethyl ether. The organic layer was washed with water and saturated saline, dried over anhydrous magnesium sulfate and anhydrous sodium sulfate, and concentrated under reduced pressure. The residue was purified by silica gel column chromatography (hexane) and vacuum distillation to give 24.6 g of 4-methoxymethoxyphenyltrimethyltin as a colorless oil (yield 89%, bp. 97°–102° C./0.9 mmHg).

$^1$H-NMR (CDCl$_3$:δ) 0.27 (9H, s, SnCH$_3$), 3.48 (3H, s, OCH$_3$), 5.19 (2H, s, OCH$_2$O), 7.05 (2H, d, J=9 Hz, Aromatic 3, 5-H), 7.42 (2H, d, J=9 Hz, Aromatic 2, 6-H).

(c) 20 g (66.5 mmol) of the tin compound obtained in the above (b) was dissolved in 40 ml of anhydrous acetonitrile, 8.4 g (100 mmol) of anhydrous sodium carbonate was added, and 10 g (100 mmol) nitrosonium tetrafluoroborate was added under an argon stream and cooling to −78° C. and stirring. After the addition, the mixture was stirred at 0° C. for 1 hour. After the reaction, the reaction solution was diluted with diethyl ether, and the organic layer was washed successively with saturated sodium bicarbonate solution, water and saturated saline, dried over anhydrous magnesium sulfate and anhydrous sodium sulfate, and concentrated under reduced pressure. The residue was purified by silica gel column chromatography (diethyl ether-hexane=4:1) to give 6.1 g of 4-methoxymethoxynitrosobenzene as a blue oil (yield 55%, bp. 75°–78° C./3 mmHg).

$^1$H-NMR (CDCl$_3$:δ) 3.51 (3H, s, OCH$_3$), 5.30 (2H, s, OCH$_2$O ), 7.18 (2H, d, J=9 Hz, Aromatic 3, 5-H), 7.91 (2H, d, J=9 Hz, Aromatic 2, 6-H).

(d) 32 mg (0.3 mmol) of the nitrosobenzene compound obtained in the above (c) was dissolved in 1 ml of acetonitrile, and 24 mg (0.33 mmol) of cis-3-amino-2-butanol obtained in Reference example 3 (a) was added. Under ice cooling, a solution of 168 mg (0.66 mmol) of iodine in 2 ml of acetonitrile was added, 0.65 ml of antiformine (corresponding to 0.44 mmol of sodium hypochlorite) was then added, and after completion of the dropwise addition, the mixture was stirred for further 1 hour. After the reaction, 1.5 ml of 1M sodium thiosulfate solution was added, followed by extraction with diethyl ether. The organic layer was washed successively with 1M sodium thiosulfate solution, saturated ammonium chloride solution and saturated saline, dried over anhydrous sodium sulfate, and concentrated under reduced pressure. The residue was purified by silica gel column chromatography (diethyl ether-hexane=1:20) to give 16.6 mg of the desired compound as a colorless oil (yield 43%).

$^1$H-NMR (CDCl$_3$:δ) 1.22 (3H, d, J=6 Hz, 4-CH$_3$), 1.28 (3H, d, J=6 Hz, 1-CH$_3$), 2.23 (1H, br. s, OH), 3.49 (3H, s, OCH$_3$), 3.99 (1H, quint., J=6 Hz, 2-CH), 4.18 (1H, quint., J=6 Hz, 3-CH), 5.23 (2H, s, OCH$_2$O), 7.07 (2H, d, J=9 Hz, Aromatic 3, 5-H), 8.11 (2H, d, J=9 Hz, Aromatic 2, 6-H).

I R:ν max, CHCl$_3$, cm$^{-1}$ 3440, 1595, 1495, 1465, 1305, 1220.

Example 8

Preparation of 3-(4-hydroxyphenyl-ONN-azoxy)-2-butanol 16.6 mg (0.0654 mmol) of the condensed compound obtained in Example 7 was dissolved in 1.0 ml of tetrahydrofuran, 0.3 ml of concentrated hydrochloric acid was added under ice cooling, and the mixture was brought back to room temperature and stirred for 30 minutes. After the reaction, 10N sodium hydroxide solution was added to the reaction solution to make the pH 6, followed by extraction with ethyl acetate. The organic layer was washed with saturated saline, dried over anhydrous sodium sulfate, and concentrated under reduced pressure. The residue was purified by silica gel column chromatography (diethyl ether-hexane=3:2→diethyl ether), and recrystallized from chloroform-hexane to give 12.6 mg of the desired compound as colorless needles (mp. 124°–125° C. yield 92%).

$^1$H-NMR (CD$_3$COCD$_3$:δ) 1.15 (3H, d, J=7 Hz, 4-CH$_3$), 1.20 (3H, d, J=6 Hz, 1-CH$_3$), 3.95 (1H, br. quint., J=6 Hz, 2-CH), 4.17 (1H, quint., J=7 Hz, 3-CH), 6.92 (2H, d, J=9 Hz, Aromatic 3, 5-H), 8.07 (2H, d, J=9 Hz, Aromatic 2, 6-H).

IR value:ν max, CHCl$_3$, cm$^{-1}$ 3320, 3170, 1615, 1475, 1325, 1300, 1250.

Example 9

Preparation of 3-(4-methoxyphenyl-ONN-azoxy)-2-butanol 9.4 mg (0.045 mmol) of the phenol compound obtained in Example 8 was dissolved in 0.2 ml of anhydrous dimethylformamide, 0.025 ml (0.4 mmol) of methyl iodide and 12.3 mg (0.089 mmol) of potassium carbonate were added, and the mixture was stirred at room temperature for 1 hour. After the reaction, ethyl acetate was added to the reaction solution, and the organic layer was washed successively with saturated saline, saturated ammonium chloride solution and saturated saline, dried over anhydrous sodium sulfate, and concentrated under reduced pressure. The residue was purified by silica gel preparative thin layer chromatography (diethyl ether-hexane =1:2) to give 8.5 mg of the desired compound as a colorless oil (yield 90%).

$^1$H-NMR (CDCl$_3$:δ) 1.23 (3H, d, J=6 Hz, 4-CH$_3$), 1.28 (3H, d, J=6 Hz, 1-CH$_3$), 2.20 (1 H, br, s, OH), 3.88 (3H, s, OCH$_3$), 3.93–4.08 (1H, m, 2-CH), 4.18 (1H, quint., J=6 Hz, 3-CH), 6.93 (2H, d, J=9 Hz, Aromatic 3, 5-H), 8. 12 (2H, d, J=9 Hz, Aromatic 2, 6-H).

I R:ν max, CHCl$_3$, cm$^{-1}$ 3440, 1595, 1495, 1465, 1325, 1255.

Example 10

Preparation of 3-(4-(2-propynyloxy)phenyl-ONN-azoxy)-2-butanol 8.8 mg (0.042 mmol) of the phenol compound obtained in Example 8 was dissolved in 0.5 ml of anhydrous dimethylformamide, 0.021 ml (0.24 mmol) of propargyl bromide and 7 mg (0.05 mmol) of anhydrous potassium carbonate were added at room temperature, and the mixture was stirred for 3 hours. After the reaction, water was added to the reaction solution, followed by extraction with diethyl ether. The organic layer was washed with saturated ammonium chloride solution and saturated saline, dried over anhydrous sodium sulfate, and concentrated under reduced pressure. The residue was purified by silica gel column chromatography (diethyl ether-hexane=2:3) to give 8.2 mg of the desired compound as a colorless oil (yield 80%).

$^1$H-NMR (CDCl$_3$:δ) 1.22 (3H, d, J=7 Hz, 4-CH$_3$), 1.28 (3H, d, J=6 Hz, 1-CH$_3$), 2.18 (1H, br. s, OH), 2.56 (1H, t, J=2 Hz, ≡CH), 3.88–4.07 (1H, m, 2-CH), 4.18 (1H, quint., J=7 Hz, 3-CH), 4.76(2H, d, J=2 Hz, ≡CCH$_2$O), 7.02(2H, d, J =9Hz, Aromatic 3, 5-H), 8.13 (2H, d, J=9 Hz, Aromatic 2, 6-H).

I R:ν max, CHCl$_3$, cm$^{-1}$ 3470, 3290. 1595, 1495. 1465, 1300, 1230.

Example 11

Preparation of 3-(4-(3-iodo-2-propynyloxy)phenyl-ONN-azoxy)-2-butanol 16 mg (0.064 mmol) of iodine was dissolved in 0.16 ml of methanol, a methanol (0.02 ml) solution of 6.3 mg (0.025 mmol) of the propynyl compound obtained in Example 10 and 0.005 ml (0.05 mmol) of 10N sodium hydroxide solution were added under ice cooling, and the mixture was brought back to room temperature and stirred for 45 minutes. Further 0.002 ml of 10N sodium hydroxide solution was added to the reaction solution, followed by stirring for 10 minutes. After the reaction, the reaction solution was neutralized with addition of hydrochloric acid, concentrated under reduced pressure to remove part of the solvent, and extracted with ethyl acetate. The organic layer was washed successively with saturated saline, 1M sodium thiosulfate and saturated saline, dried over anhydrous sodium sulfate, and concentrated under reduced pressure. The residue was purified by silica gel preparative thin layer chromatography (ethyl acetate-benzene=1:20) to give 7.3 mg of the desired compound as a colorless oil (yield 77%).

$^1$H-NMR (CDCl$_3$:δ) 1.23 (3H, d,J=6 Hz, 4-CH$_3$) , 1.28 (3H, d,J=6 Hz, 1CH$_3$), 2.17 (1H, br. d, J=6 Hz, OH), 3.99 (1H, br. quint., J=6 Hz, 2-CH), 4.18 (1H, quint., J=6 Hz, 3-CH), 4.90 (2H, s, OCH$_2$), 7.00 (2H, d, J=9 Hz, Aromatic 3.5-H), 8.13 (2H, d, J=9 Hz, Aromatic 2, 6-H).

I R:ν max, CHCl$_3$, cm$^{-1}$ 3960, 1595. 1495, 1465, 1295, 1225.

Example 12

Preparation of 2(R)-3(S)-3-(4-chlorophenyl-ONN-azoxy)-2-butanol (a) A small quantity of iodine was put in a vessel containing 280 mg (12 mmol) of metal magnesium and 10 ml of anhydrous diethyl ether, and a solution of 2.0 g (10 mmol)

of 4-bromobenzene in 10 ml of anhydrous diethyl ether was gradually added dropwise under stirring. Reaction progressed rapidly, and after the reaction somewhat calmed down, the mixture was heated and stirred at 50° C. for further 3 hours. Thereafter, the reactor was cooled to 0° C., 2.1 g (10 mmol) of trimethyltin chloride was added, and the mixture was heated again to 50° C. and refluxed for 2 hours. After the reaction, the reaction solution was cooled again to 0° C., saturated ammonium chloride solution was added, and the mixture was extracted with diethyl ether. The organic layer was washed with water and saturated saline, dried over anhydrous magnesium sulfate and anhydrous sodium sulfate, and concentrated under reduced pressure. The residue was purified by silica gel column chromatography (hexane) and vacuum distillation to give 1.9 g of 4-chlorophenyltrimethyltin as a colorless oil (yield 64%).

$^1$H-NMR (CDCl$_3$:δ) 0.29 (9H, s, SnCH$_3$), 7.31 (2H, d, J=8.8 Hz, Aromatic H), 7.39 (2H, d, J=8.8 Hz. Aromatic H).

(b) 1.85 g (6.7 mmol) of the tin compound obtained in the above (a) was dissolved in 13 ml of anhydrous methylene chloride, and 1.1 g (9.4 mmol) of nitrosonium tetrafluoroborate was added under an argon stream and cooling to −78° C. and stirring. After the addition, the mixture was stirred at 0° C. for 1 hour. After the reaction, the reaction solution was diluted with diethyl ether, and the organic layer was washed successively with saturated sodium bicarbonate solution, water and saturated saline, dried over anhydrous magnesium sulfate and anhydrous sodium sulfate, and concentrated under reduced pressure. The residue was purified by silica gel column chromatography (diethyl ether-hexane =4:1), and then recrystallized from chloroform-hexane to give 390 mg of 4-choronitrosobenzene as pale yellow crystals (yield 41%).

$^1$H-NMR (CDCl$_3$:δ) 7.60 (2H, d. J=8.8 Hz, 3, 5-Aromatic H), 7.85 (2H, d, J=8.8 Hz, 2, 6-Aromatic H).

I R:ν max, CHCl$_3$, cm$^{-1}$ 1491, 1113, 1085, 906, 831.

(c) 80 mg (0.39 mmol) of the silylamine compound obtained in Reference example 4 was dissolved in 1 ml of anhydrous acetonitrile, the solution was cooled to 0° C., and 200 mg (0.78 mmol) of iodine was added to dissolve the silylamine compound completely. 55 mg (0.39 mmol) of 4-chloronitrosobenzene obtained in the above (b) and 0.09 ml (0.78 mmol) of tert-butyl hypochlorite were successively added thereto, and the mixture was stirred for 3 hours. After the reaction, the reaction solution was diluted with diethyl ether, and the organic layer was washed with saturated sodium thiosulfate solution and saturated saline, dried over anhydrous magnesium sulfate and anhydrous sodium sulfate, and concentrated under reduced pressure. The residue was purified by silica gel column chromatography (hexane) to give 54 mg of a condensed compound (2R)-(3S)-3-(4-chlorophenyl-ONN-azoxy)-2-(tert-butyldimethylsilyloxy)butane as a pale yellow oil (yield 45%).

$^1$H-NMR (CDCl$_3$:δ) 0.05 (3H, s, SiCH$_3$), 0.06 (3H, s, SICH$_3$), 0.89 (9H, s, Si-t-Bu), 1.20 (3H, d, J=6.4 Hz, 1 or 4-CH$_3$), 1.22 (3H, d, J=6.4 Hz, 1 or 4-CH$_3$), 4.00–4.10 (1H, m, 2 or 3-CH), 4.13–4.23 (1H, m, 2 or 3-CH), 7.42 (2H, d, J=9 Hz, 3, 5-Aromatic H), 8.19 (2H, d, J=9 Hz, 2, 6-Aromatic H).

(d) 50 mg (0.16 mmol) of the condensed compound obtained in the above (c) was dissolved in 0.3 ml of ethanol, the solution was cooled to 0° C., 0.15 ml of 6 N hydrochloric acid was added, and the mixture was stirred at room temperature for 90 minutes. After the reaction, the reaction solution was diluted with ethyl acetate, and the organic layer was washed successively with saturated sodium bicarbonate solution and saturated saline, dried over anhydrous magnesium sulfate and anhydrous sodium sulfate, and concentrated under reduced pressure. The residue was purified by silica gel column chromatography (diethyl ether-hexane= 1:2) to give 27 mg of the desired compound as a pale yellow oil (yield 76%).

$^1$H-NMR (CDCl$_3$:δ) 1.25 (3H, d, J=6.4Hz, 1 or 4-CH$_3$), 1.29 (3H, d, J=6.4 Hz, 1 or 4-CH$_3$), 1.98 (1H, br. d, J=3.9 Hz, OH), 4.02–4.11 (1H, m, 2-CH) , 4.26–4.35 (1H, m, 3-CH), 7.44 (2H, d, J=9 Hz, 3, 5-Aromatic H), 8.11 (2H, d, J=9 Hz, 2, 6-Aromatic H) .

I R:ν max, CHCl$_3$, cm$^{-1}$ 1468, 1306, 1090.

Example 13

Preparation of 2(R)-3(S)-3-(4-bromophenyl-ONN-azoxy)-2-butanol (a) 3.0 g (13 mmol) of p-dibromobenzene was dissolved in 100 ml of anhydrous diethyl ether, and under room temperature and an argon stream, 8.0 ml (13 mmol) of 1.6M n-butyllithium (hexane solution) was gradually added dropwise, followed by stirring for 1 minute. Further, 2.8 g (14 mmol) of trimethyltin chloride was added, and refluxed at 50° C. for 2 hours. After the reaction, the reaction solution was cooled, saturated ammonium chloride solution was added, and the mixture was extracted with diethyl ether. The organic layer was washed successively with water and saturated saline, dried over anhydrous magnesium sulfate and anhydrous sodium sulfate, and concentrated under reduced pressure. The residue was purified by silica gel column chromatography (hexane) to give 2.7 g of 4-bromophenyltrimethyltin as a colorless oil (yield 66%).

$^1$H-NMR (CDCl$_3$:δ) 0.29 (9H, s, SnCH$_3$), 7.34 (2H, d, J=8.3 Hz), 7.47 (2H, d, J=8.3 Hz).

(b) 2.7 g (8 mmol) of the tin compound obtained in the above (a), 16 ml of anhydrous methylene chloride and 1.2 g (11 mmol) of nitrosonium tetrafluoroborate were subjected to reaction, treatment and purification in the same manner as in Example 7 (c) to give 1.11 g of 4-bromonitrosobenzene as pale yellow crystals (yield 71.0%).

$^1$H-NMR (CDCl$_3$:δ) 7.78 (4H, s, Aromatic H).

(c) 170 mg (0.8 mmol) of the silylamine compound obtained in Reference example 4, 150 mg (0.8 mmol) of 4-bromonitrosobenzene obtained in the above (b), 400 mg (1.6 mmol) of iodine, 0.19 ml (1.6 mmol) of tert-butyl hypochlorite and 2.5 ml of anhydrous acetonitrile were subjected to reaction and treatment in the same manner as in Example 12 (c) to give 190 mg of a condensed compound (2R)-(3S)-3-(4-bromophenyl-ONN-azoxy)-2-(tert-butyldimethylsilyloxy)butane as pale yellow crystals.

$^1$H-NMR (CDCl$_3$:δ) 0.05 (3H, s, SiCH$_3$), 0.06 (3H, s, SiCH$_3$), 0.89 (9H, s, Si-t-Bu), 1.20 (3H, d, J=7 Hz, 1 or 4-CH$_3$), 1.22 (3H, d, J=7 Hz, 1 or 4-CH$_3$), 4.00–4.09 (1H, m, 2 or 3-CH), 4.13–4.22 (1H, m, 2 or 3-CH), 7.58 (2H, d, J=9 Hz, 3, 5-Aromatic H), 8.03 (2H, d, J=9 Hz, 2, 6-Aromatic H).

(d) 190 mg of the crudely purified condensed compound obtained in the above (c), 1 ml of ethanol and 0.5 ml of 6N hydrochloric acid were subjected to reaction, treatment and purification in the same manner as in Example 12 (d) to give 80 mg of the desired compound as pale yellow oil (yield 37%).

$^1$H-NMR (CDCl$_3$:δ) 1.24 (3H, d, J=6.4 Hz, 1 or 4-CH$_3$), 1.28 (3H, d, J=6.4 Hz, 1 or 4-CH$_3$), 4.01–4.10 (1H, m, 2-CH), 4.25–4.34 (1H, m, 3-CH), 7.60 (2H, d, J=9 Hz,

21

3, 5-Aromatic H), 8.04 (2H, d, J=9 Hz, 2,6-Aromatic H).

I R:ν max, CHCl₃, cm⁻¹ 1466, 1296, 1066, 1009.

Example 14

Preparation of 2(R)-3(S)-3-(4-fluorophenyl-ONN-azoxy)-2-butanol (a) 3.0 g (13 mmol) of 4-fluorobromobenzene, 100 ml of anhydrous diethyl ether, 12 ml (19 mmol) of 1.6 M n-butyllithium (hexane solution) and 3.8 g (19 mmol) of trimethyltin chloride were subjected to reaction, treatment and purification in the same manner as in Example 13 (a) to give 970 mg of 4-flurophenyltrimethyltin as a colorless oil (yield 22%).

¹H-NMR (CDCl₃, δ) 0.29 (9H, s, SnCH₃), 7.05 (2H, dd, J=9.8 Hz, 8.8 Hz, Aromatic 3, 5-H), 7.44 (2H, dd, J=8.8 Hz, 6.3 Hz, Aromatic 2, 6-H)

(b) 970 mg (4 mmol) of the tin compound obtained in the above (a), 7 ml of anhydrous methylene chloride and 600 mg (5 mmol) of nitrosonium tetrafluoroborate were subjected to reaction, treatment and purification in the same manner as in Example 7 (c) to give 280 mg of 4-fluoronitrosobenzene as pale yellow crystals (yield 59.0%).

¹H-NMR (CDCl₃, δ) 7.05 (2H, dd, J=8.8 Hz, 7.8 Hz, Aromatic 3, 5-H), 7.96 (2H, dd, J=8.8 Hz, 5.4 Hz, Aromatic 2, 6-H).

I R:ν max, CHCl₃, cm⁻¹ 1596, 1505, 1230, 1110.

(c) 460 mg (2.2 mmol) of the silylamine compound obtained in Reference example 4, 280 mg (2.2 mmol) of the above nitroso compound, 6 ml of anhydrous acetonitrile, 1.1 g (4.5 mmol) of iodine and 0.53 ml (4.5 mmol) of tert-butyl hypochlorite were subjected to reaction, treatment and purification in the same manner as in Example 12 (c) to give 320 mg of a condensed compound (2R)-(3S)-3-(4-fluorophenyl-ONN-azoxy)-2-(tert-butyldimethylsilyloxy)butane as a pale yellow oil (yield 43%).

¹H-NMR (CDCl₃, δ) 0.05 (3H, s, SiCH₃), 0.07 (3H, s, SiCH₃), 0.90 (9H, s, Si-t-Bu), 1.20 (3H, d, J=6.4 Hz, 1 or 4-CH₃), 1.22 (3H, d, J=6.4 Hz, 1 or 4-CH₃), 4.01–4.10 (1H, m, 2-CH), 4.14–4.23 (1H, m, 3-CH), 7.12 (2H, dd, J=9.3 Hz, 4.9 Hz, Aromatic 3, 5-H), 8.17 (2H, dd, J=9.3 Hz, 8.3 Hz, Aromatic 2, 6-H).

I R:ν max, CHCl₃, cm⁻¹ 2924, 1468, 1218, 1140, 1110, 1086.

(d) 320 mg (0.96 mmol) of the condensed compound obtained in the above (c), 2 ml of ethanol and 1.0 ml of 6N hydrochloric acid were subjected to reaction, treatment and purification in the same manner as in Example 12 (d) to give 200 mg of the desired compound as a pale yellow oil (yield 98%).

¹H-NMR (CDCl₃, δ) 1.25 (3H, d, J=6.4 Hz, 1 or 4-CH₃), 1.29 (3H, d, J=6.4 Hz, 1 or 4 -CH₃), 2.05 (1 H, br. s, OH), 4.02–4.11 (1H, m, 2-CH), 4.26–4.35 (1H, m, 3-CH), 7.14 (2H, dd, J=9.3 Hz, 4.9 Hz, Aromatic 3, 5-H), 8.18 (2H, dd, J=9.3 Hz, 7.8 Hz, Aromatic 2, 6-H).

I R:ν max, CHCl₃, cm⁻¹ 1595, 1491, 1300, 1234, 1149.

Example 15

Preparation of 2(R)-3(S)-3-(4-hydroxyphenyl-ONN-azoxy)-2-butanol 820 mg (4.89 mmol) of the nitrosobenzene obtained in Example 7 (c), 1 g (4.89 mmol) of the silylamine obtained in Reference example 4, 1.17 ml (9.78 mmol) of tert-butyl hypochlorite, 2.48 g (9.78 mmol) of iodine, and 40 ml of benzene in place of acetonitrile were subjected to reaction and treatment in the same manner as in Example 12 (c), and the resultant crude condensed compound (2R)-(3S )-3-(4-methoxymethoxyphenyl-Onn-azoxy)-2 -(tert-butyldimethylsilyloxy)butane was subjected to deprotection according to Example 8 using 15 ml of tetrahydrofuran and 3 ml of concentrated hydrochloric acid to give 750 mg of the desired compound as a colorless oil (yield 73%).

¹H-NMR (CDCl₃, δ) 1.24 (3H, d, J=7 Hz, 4-CH₃), 1.32 (3H, d, J=6Hz, 1-CH₃), 2.61 (1H, br. s, OH), 4.04–4.17 (1H, m, 2-CH), 4.36 (1H, dq, J=4 Hz, 7 Hz, 3-CH), 6.83 (2H, d, J=9 Hz, Aromatic 3, 5-H), 6.99 (1H, br. s, OH) , 7.99 (2H, d, J=9 Hz, Aromatic 2, 6-H) .

I R:ν max, CHCl₃, cm⁻¹ 3420, 1615, 1475, 1280, 1165.

Example 16

Preparation of 2(R)-3(S)-3-(4-(2-propynyloxy)phenyl-ONN-azoxy)-2-butanol 2.96 g (14.0 mmol) of the hydroxy compound obtained in Example 15 was dissolved in 16 ml of anhydrous dimethylformamide, 7.0 ml (79 mmol) of propargyl bromide and 2.18 g (158 mmol) of anhydrous potassium carbonate were added at room temperature, and the mixture was stirred for 3 hours. After the reaction, 10 ml of water was added to the reaction solution, followed by extraction with diethyl ether. The organic layer was washed with saturated ammonium chloride solution and saturated saline, dried over anhydrous sodium sulfate, and concentrated under reduced pressure. The residue was purified by silica gel column chromatography (diethyl ether-hexane=2:3) to give 3.19 g of the desired compound as a colorless oil (yield 91%).

¹H-NMR (CDCl₃, δ) 1.24 (3H, d, J=6 Hz, 4-CH₃), 1.28 (3H, d, J=7 Hz, 1-CH₃), 2.19 (1H, br. s, OH), 2.56 (1H, t, J=2 Hz, ≡CH), 3.98–4.12 (1H, m, 2-CH), 4.31 (1 H, dq, J=4 Hz, 6 Hz, 3-CH), 4.76 (2H, d, J=2 Hz, ≡32 CCH₂O), 7.01 (2H, d, J=9 Hz, Aromatic 3, 5-H), 8.13 (2H, d, J=9 Hz, Aromatic 2, 6-H).

I R:ν max, CHCl₃, cm⁻¹ 3430, 3290, 1595, 1495, 1465, 1295, 1230, 1190.

Example 17

Preparation of 2(R)-3(S)-3-(4-(3-iodo-2-propynyloxy)phenyl-ONN-azoxy)-2-butanol 7.97 g (31.42 mmol) of iodine was dissolved in 150 ml of methanol, 3.9 g (15.71 mmol) of the propynyl compound obtained in Example 16 and 5.3 ml (53 mmol) of 10N sodium hydroxide solution were added under ice cooling, and the mixture was brought back to room temperature and stirred for 1 hour. After the reaction, saturated sodium thiosulfate was added to the reaction solution, part of the solvent was distilled off under reduced pressure, and the resultant solution was extracted with ethyl acetate. The organic layer was washed successively with saturated saline, 1M sodium thiosulfate and saturated saline, dried over anhydrous sodium sulfate, and concentrated under reduced pressure. The residue was purified by silica gel column chromatography (diethyl ether-hexane=2:1) to give 5.65 g of the desired compound as colorless crystals (mp. 62°–64° C., yield 82%).

¹H-NMR (CDCl₃, δ) 1.24 (3H, d, J=6 Hz, 4-CH₃), 1.29 (3H, d, J=6 Hz, 1-CH₃), 2.12 (1H, br. s, OH), 3.98–4.12 (1H, m, 2-CH), 4.31 (1H, dq, J=4 Hz, 6 Hz, 3-CH), 4.89

(2H, s, ≡CCH₂O), 7.00 (2H, d, J=9 Hz, Aromatic 3, 5-H), 8.13 (2 H, d, J=9 Hz, Aromatic 2, 6-H).

I R:ν max, CHCl₃, cm⁻¹ 3440, 1595, 1495, 1465, 1295, 1225, 1170.

Formulation example 1
Cream preparation for administration to human beings:

| | |
|---|---|
| Compound of (2R) of Example 5 | 2.0 g |
| White petrolatum | 25.0 |
| Stearyl alcohol | 25.0 |
| Propylene glycol | 12.0 |
| Sodium lauryl sulfate | 1.5 |
| Ethyl paraoxybenzoate | 0.5 |
| Deionized water | 34.0 |

The above mixture was uniformly mixed according to a conventional method to give a cream.

Formulation example 2
Capsules for administration to human beings:

| | |
|---|---|
| Compound of Example 17 | 500 g |
| microcrystalline cellulose | 90 |
| Talc | 30 |

The above mixture was uniformly mixed according to a conventional method, and packed into 1,000 No. 0 capsules.

Formulation example 3
Agrohorticultural emulsifiable concentrate:

| | |
|---|---|
| Compound of (2S) of Example 5 | 250 g |
| Epoxidized vegetable oil | 25 |
| Mixture of alkylaryl sulfonate, polyglycol ether and fatty alcohol | 100 |
| Dimethylformamide | 50 |
| Xylene | 575 |

The above mixture was uniformly mixed according to a conventional method to give an emulsifiable concentrate. When used, this is diluted with water to give an emulsion.

We claim:

1. An azoxy compound represented by the following general formula

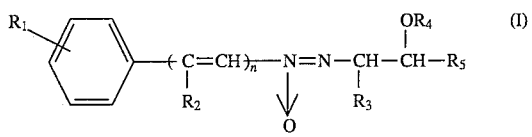

wherein

R₁ denotes I—C≡C—CH₂O—;

R₂ denotes a hydrogen atom or a lower alkyl group;

R₃ denotes a lower alkyl group;

R₄ denotes a hydrogen atom or a group of the formula X₂—C≡C—CH₂— wherein X₂ is a hydrogen atom or a halogen atom;

R₅ denotes a hydrogen atom or a lower alkyl group; and n is 0 or 1.

2. The compound according to claim 1 represented by the formula

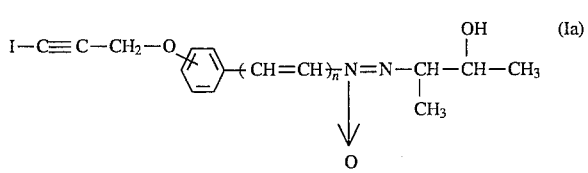

wherein n is 0 or 1.

3. The compound according to claim 1 which is 3-(4-(3-iodo-2-propynyloxy)styryl-ONN-azoxy)-2-butanol, or 3-(4-(3-iodo-2-propynyloxy)phenyl-ONN-azoxy)-2butanol.

4. An antifungal agent containing the azoxy compound according the claim 1.

5. An antifungal composition comprising the azoxy compound according to claim 1 and pharmaceutically acceptable auxiliaries.

6. A method for treatment of a mycetogenic infectious disease of a warm-blooded animal which comprises administering an effective quantity of the azoxy compound according to claim 1 to the warm-blooded animal.

7. A method for treatment of an agrohorticultural crop or a fruit tree infected with fungi which comprises applying the azoxy compound of claim 1 to an area where the fungi live.

* * * * *